United States Patent
Sanjuan et al.

(10) Patent No.: US 8,390,446 B2
(45) Date of Patent: Mar. 5, 2013

(54) METHOD AND APPARATUS FOR ON-LINE ESTIMATION AND FORECASTING OF SPECIES CONCENTRATION DURING A REACTION BY MEASURING ELECTRICAL CONDUCTIVITY

(75) Inventors: Marco E. Sanjuan, Puerto Colombia (CO); Jaime R. Garcia, Puerto Colombia (CO); Jose D. Posada, Puerto Colombia (CO); Pedro J. Villalba, Puerto Colombia (CO)

(73) Assignee: Fundacion Universidad del Norte, Barranquilla (CO)

( * ) Notice: Subject to any disclaimer, the term of this patent is extended or adjusted under 35 U.S.C. 154(b) by 699 days.

(21) Appl. No.: 12/608,180

(22) Filed: Oct. 29, 2009

(65) Prior Publication Data

US 2010/0109893 A1 May 6, 2010

Related U.S. Application Data

(60) Provisional application No. 61/109,909, filed on Oct. 30, 2008.

(51) Int. Cl.
*G08B 21/00* (2006.01)

(52) U.S. Cl. .............................. 340/540; 340/999; 137/3

(58) Field of Classification Search .................. 340/540, 340/657, 999; 137/3; 423/485
See application file for complete search history.

(56) References Cited

U.S. PATENT DOCUMENTS

| | | | |
|---|---|---|---|
| 6,350,426 B1 * | 2/2002 | Sota et al. | 423/485 |
| 7,404,411 B2 * | 7/2008 | Welch et al. | 137/3 |

FOREIGN PATENT DOCUMENTS

| | | |
|---|---|---|
| DE | 4006689 A1 | 8/1991 |
| DE | 4227727 A1 | 2/1994 |
| GB | 2165360 A | 4/1986 |
| WO | 0212129 A1 | 2/2002 |

OTHER PUBLICATIONS

Aguado, D., et al., "Process Understanding of a Wastewater Batch Reactor with Block-Wise PLS," Environmentrics, vol. 18, pp. 551-560, 2007.

Neumann, Joachim, et al., "Fault Detection and Diagnosis in Chemical Plants Using Neural Agents," Chem. Eng.Technol., vol. 26, No. 12, pp. 1241-1246, 2003.

Written Opinion of the International Searching Authority for PCT International Patent Application No. PCT/IB2009/007398, mailed Sep. 10, 2010.

PCT International Search Report for PCT International Patent Application No. PCT/IB2009/007398, mailed Sep. 10, 2010.

* cited by examiner

*Primary Examiner* — Jeffery Hofsass
(74) *Attorney, Agent, or Firm* — Holland & Hart LLP

(57) ABSTRACT

A method and apparatus for on-line measurement and forecasting of a species concentration while a reaction is taking place, based on the measurement of the electrical conductivity of the reacting volume, and using such measurement to evaluate a first mathematical function relating such value to the concentration of the species in the reacting volume. The evaluation of the first mathematical function requires as inputs: electrical conductivity trajectory, time elapsed, and other significant process variables; it generates as outputs the estimated actual species concentration and at least one forecasted concentration value.

21 Claims, 3 Drawing Sheets

METHOD AND APPARATUS FOR ON-LINE ESTIMATION AND FORECASTING OF SPECIES CONCENTRATION DURING A REACTION BY MEASURING ELECTRICAL CONDUCTIVITY

CROSS-REFERENCE TO RELATED APPLICATION

This application claims the benefit of the filing date of U.S. Provisional Application No. 61/109,909, filed Oct. 30, 2008, and entitled METHOD AND APPARATUS FOR ON-LINE ESTIMATION AND FORECASTING OF SPECIES CONCENTRATION DURING A REACTION, the disclosure of which is incorporated, in its entirety, by this reference.

BACKGROUND OF THE INVENTION

Measuring concentration is not an easy task in engineering and process practice. Most concentration (or analysis) sensors are designed specifically for certain type of species. Other general methods, such as chromatography and spectroscopy, require sampling and laboratory analysis hence are not suitable for on-line measurement of the concentration.

Some works that measure concentration using indirect measurement variables can be listed as follows:
- Concentration distribution in a fluid by electric impedance tomography [Ijaz et. al., 2007]
- Lactic acid concentration estimation in fermentation broth by conductivity measurement, [Payot et. al., 1997]
- Method for determining component concentration in three-component mixture, [Sota et. al., 2002], U.S. Pat. No. 6,350,426.
- Method and apparatus for analyzing chemical composition, [Markant et. al., 1970], U.S. Pat. No. 3,537,820
- Arrangement for determining concentration of measurement liquid with neural network based on conductivity, [Schwulera and Riegel, 2000], German Patent Office, DE 198 35 137 A 1.

Out of the previous methods, numbers 2 and 5 use conductivity, however in a non-dynamic way, and based on a direct data-driven inference, which makes them radically different from the approach taken in this invention.

When the task of measuring concentration is focused in a chemical reactor, it becomes even more challenging, since concentration exhibits a dynamic behavior that most sensors are not capable of taking into account.

So far, common production practices and technology call for off-line sample analysis from the product stream, and the reacting volume is monitored for operational variables such as temperature and pressure, but not for product quality purposes. Product stream analysis is performed by sampling every often and taking those samples to a laboratory.

Lately, some estimation methods have been developed to monitor a progressing reaction based on the use of in-situ viscometer [Elli, et. al., 2007] and fiber-optic near-infrared (NIR) spectroscopy [Knothe, 2000]. Later, the NIR method by Knothe was used to measure biodiesel content in a hydrocarbons mixture, useful in blending applications, as presented on U.S. Pat. No. 7,404,411. Using a viscometer requires adding a moving element into the reaction vessel. NIR spectroscopy is a very expensive technology, not always suitable for the plant floor, and it also requires a well trained operator. Also, the methods presented in the literature, do not explicitly take into account dynamic behavior.

An unfulfilled need addressed by the present invention is to provide an automated method and a non-moving apparatus to measure species concentration in the reaction vessel based on a variable measurement easily understood by the process operators and technicians.

SUMMARY OF THE INVENTION

The present invention provides a method and apparatus for on-line measurement and forecasting of a species concentration while a reaction is taking place, based on the measurement of the electrical conductivity of the reacting volume, and using such measurement to evaluate a first mathematical function relating such value to the concentration of the species in the reacting volume. The evaluation of the first mathematical function requires as inputs: electrical conductivity trajectory, time elapsed, and other significant process variables; it generates as outputs the estimated actual species concentration and at least one forecasted concentration value.

This method and apparatus also provides an alarm based on the electrical conductivity measurement and a second mathematical function to indicate that the reaction is deviating from the desired behavior to another reaction pattern.

The present invention allows engineers in production processes to measure the concentration of reacting species in a simpler, faster, and easier to implement way. This is because electrical conductivity measurement requires no moving parts and is easier to implement than analytical techniques such as NIR. In addition, the invention allows manufacturers to improve quality control of the process by means of the warning signal generated by the deviation function.

The apparatus conceived in this invention may contain any combination of electrical conductivity sensor, display, keyboard, communication interface, other analog/digital inputs, other analog/digital outputs, processing unit, storage unit, or power supply.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

One aspect of the present disclosure relates to a method to relate dynamic conductivity behavior to dynamic species concentration behavior, such that a first mathematical dynamic function, the estimation function, can be obtained where the conductivity trajectory, time elapsed, and other significant process variable trajectory are used to estimate the present value of the species concentration and its forecasted behavior.

Another aspect of the present disclosure relates to a method to relate dynamic conductivity behavior to dynamic species concentration behavior, such that a second mathematical dynamic function, the deviation function, can be obtained where the conductivity trajectory, time elapsed, and other significant process variable trajectory are used to provide an alarm indicating that significant deviation from the desired reaction pattern is been observed.

A still further aspect of the present disclosure relates to a system and apparatus that by using the first, second, or both mathematical functions, on-line conductivity measurement, and other significant variables measurement, estimates and forecasts species concentration in a reacting volume and generates an alarm condition of deviation from a desired reaction pattern.

Figure 1:
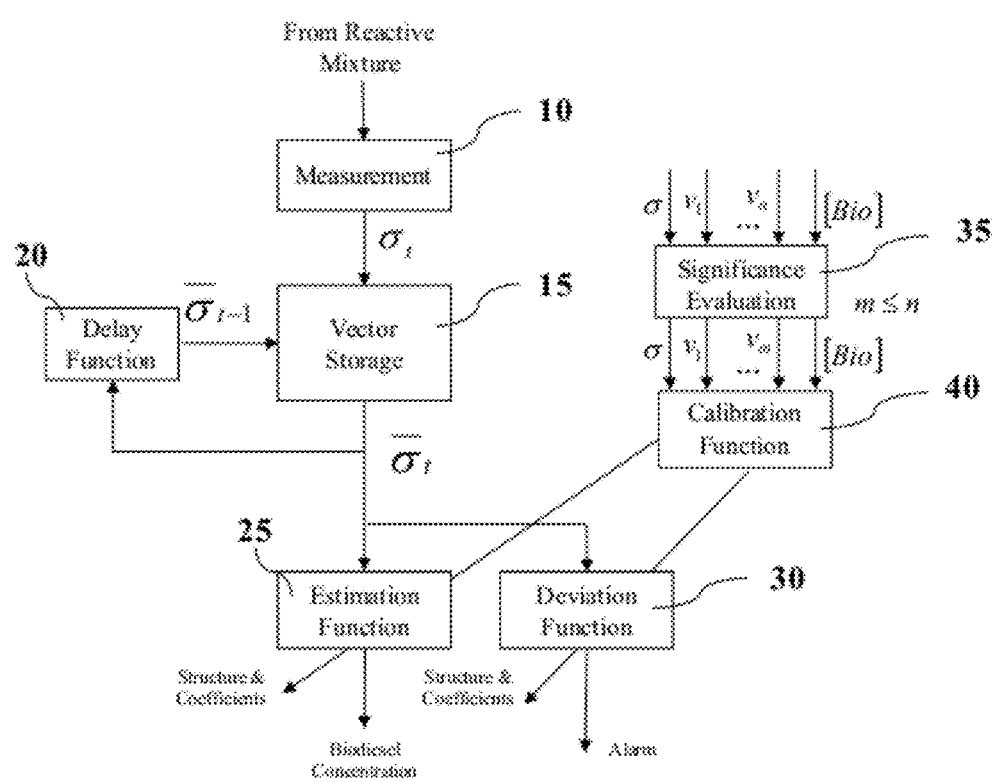
FIG. 1. Is an Illustration of the method for biodiesel concentration measurement.

The diagram describing the methods integration is presented in FIG. 1.

The electrical conductivity measures by the measurement block (10) are collected using a sensor that gives the conductivity at each sample time.

The second step is to store a vector of electrical conductivity in the storage block (15), building the conductivity trajectory, in order to feed it into the estimation function and the deviation function. This trajectory has n electrical conductivity samples and it is updated by the delay function (20) every sample time.

The estimation function (25) is determined by, for example, the following steps:
  Perform batch reactions tests
  Measure concentration, conductivity, and other significant variables in samples from the batch reactions at any possible sampling rate, generating at least 5 data points for every variable.
  Fit the reaction model kinetics coefficients that best describe the reaction.
  Fit a dynamic conductivity model.
  Simulate the dynamic models and sample from the simulation at a uniform sampling rate.
  Generate a nonlinear dynamic function relating time elapsed, t, conductivity trajectory, and other significant process variables trajectory, with species concentration at time t, and the forecasted concentration at time t+T, t+2T, ..., t+kT, where T is the sampling period and k is the maximum forecasting lag, a number equal or larger than 1.

The deviation function (30) is determined by, for example, the following steps:
  Perform batch reactions tests
  Measure concentration, conductivity, and other significant variables in samples from the batch reactions at any possible sampling rate, generating at least 5 data points for every variable.
  Fit the reaction model kinetics coefficients that best describe the reaction.
  Fit a dynamic conductivity model.
  Simulate the dynamic models and sample from the simulation at a uniform sampling rate.
  Generate a minimum and maximum stagnation time indicator based on simulated dynamic data and variance measures from batch experiments.
  Generate a pattern of dynamic reaction behavior using pattern recognition techniques.
  Generate a nonlinear dynamic hybrid function that will activate a binary state whether the stagnation time limits or the reaction pattern indicate reaction shift to an undesired trajectory.

The apparatus conceived in this invention consists at least of the following elements: a processing unit board, signal conditioning and data acquisition module board with for inputs and outputs, an electrical conductivity sensor, a communication interface, and a power supply. A computer or PLC may be used for processing and process/operator interface.

The processing unit board executes the estimation and deviation functions, and performs the steps required to calculate both functions, also called calibration. It may have routines to allow the user input the data for the calibration steps.

DETAILED DESCRIPTION OF THE PREFERRED EMBODIMENT

The invention was embodied and tested for a transesterification reaction to obtain ethyl ester (biodiesel), and biodiesel concentration was measured and forecasted using the methods and apparatus described in this invention. The diagram describing this method is presented in FIG. 1. The electrical conductivity measures by the measurement block (10) are collected using a sensor that gives the conductivity at each sample time.

The second step is to store a vector of electrical conductivity in the storage block (15), in order to feed these values into the estimation function and the deviation function. This vector has n samples from the conductivity and its actualized trough the delay function each sample time. The delay function block (20) delays the input electrical conductivity vector for the uses in the vector storage function.

The estimation function block (25) is determined using a standard feed-forward neural network with an input layer, one hidden layer and one output layer. The activation function used in the hidden layer is a sigmoid like function while in the other two layers a linear activation function is used. This function has as input the conductivity vector. This function estimates the biodiesel concentration in the reaction using the inputted information.

The deviation function block (30) is determined using a time based function that generates a warning of the undesired behavior from the reaction. This function has a model from the conductivity used to estimate the time in which the reaction has stopped or is leading to saponification reactions.

The Significance evaluation function is used in the start-up operation for the analysis of variables. This function determines which variables besides the conductivity, are useful in the identification of biodiesel concentration variations in the reaction phase. As result of this function, significant variables are selected, which are the ones explain better the process variations.

The Calibration function is used in order to modify the evaluation and deviation function, using the significant variables obtained with the significance evaluation function. This modification adjusts the functions weights and structure, to adapt them to the particular biodiesel production process.

The application of the method is described as follows:
  Calibration or start-up The method used in the estimation and deviation function requires a calibration or start up procedure in order to adjust the parameters and find the structure of each one of these functions. The necessary steps for the start-up procedure can be summarized as follows:
  Batch reactions experiments
  Concentration and conductivity measures in batch reactions.
  Determine the Kinetics coefficients for the reaction model.
  Determine the conductivity model.

In order to determine kinetic parameters, an experimental stage has to be developed. At different temperatures, a batch reactor set up shall be run, using initial concentrations of oil (vegetal, animal or wasted) and alcohol (ethanol or methanol usually). From the time the reaction starts, until equilibrium is reached samples shall be taken and their time recorded. Every sample can be taken to a HPLC or a Spectroscopy for analysis, and concentrations of reaction products recorded. Once the time path for the reaction is obtained for reacting components, a matrix of those is used to obtain the reaction constants for the kinetic model at every temperature. Reaction constant values are obtained by developing a dynamic model of the batch scenario and using non-linear optimization functions to minimize the error during the dynamic response.

The conductivity data collected trough the batch production tests are used to construct a model from the conductivity. The conductivity is approximated using an Adaptive Neuro-Fuzzy Inference System (ANFIS) trained using back-propagation based algorithm. This model is a time series. Statistical analysis can be performed in order to get the best fit for the data.

Trough the simulation of the reaction and conductivity at the same time using the models determined before, the following matrix data can be obtained:

TABLE 1

Data structure for Estimation Function calculation

| Biodiesel Concentration | Electrical Conductivity ($\sigma$) |
|---|---|
| $\sigma_1$ | $C_1$ |
| $\vdots$ | $\vdots$ |
| $\sigma_n$ | $C_n$ |

Using this input training data the estimation function was approximated using a standard feed-forward neural network with an input layer, one hidden layer and one output layer. The activation function used in the hidden layer is a sigmoid like function while in the other two layers a linear activation function were used.

The hidden layer weights were calculated using normal random numbers regularized, using the following regularization equation:

$$W^h = \sqrt{\frac{a}{\max_k \sum_{i=1}^{N_j+1} x_i^2(k)}} N(0, 1) \quad (1)$$

Where, a is the maximum input of the activation function used, xi is the training data for an input, Ni is the number of inputs, and N(0,1) is a normal random number generator with mean equal to zero and variance equal to one. The output weights (Wo) are calculated using standard least squares problem solution:

$$Z = X \times W^h \quad (2)$$

$$V = f(Z) \quad (3)$$

$$\hat{W}^o = (V_b^T V_b)^{-1} V_b^T Y \quad (4)$$

Where, X is the input training data, f is the activation function, $V_b$ is equal to V except that one column with ones is added to express output bias $b_o$, and Y is the output training data.

The optimization of neural network architecture was carried out using a greedy search modified for a multiobjective optimization procedure.

Using the same input training data and the same conductivity model obtained before, a deviation function is determined in order to warn about the undesired behavior of the reaction. This deviation function calculates the maximum time before a specific pattern of conductivity behavior must occur at the normal process reaction. In the case this pattern does not occur, an alarm is set trough a binary state, indicating one as undesired process reaction and zero as normal process reaction.

The present invention requires off-line laboratory calibration procedure to adjust the regression models (estimation function and deviation function). Data required for calibration consists of a set of samples with electrical conductivity, biodiesel concentration, and other common process variables such as temperature, pressure, level, and flow. Electrical conductivity and temperature can be measured with the apparatus described in this invention. Pressure, flow, and level can be determined by means of appropriate sensors for Biodiesel production. Off-line analytical methods such as chromatography or spectroscopy may be used to measure biodiesel concentration to comply with this start-up requirement. This information shall be used by the apparatus to automatically, or with human assistance, incorporate statistically significant variables into the mathematical functions, and estimate the correlation structure, weights, and coefficients.

Figure 2:
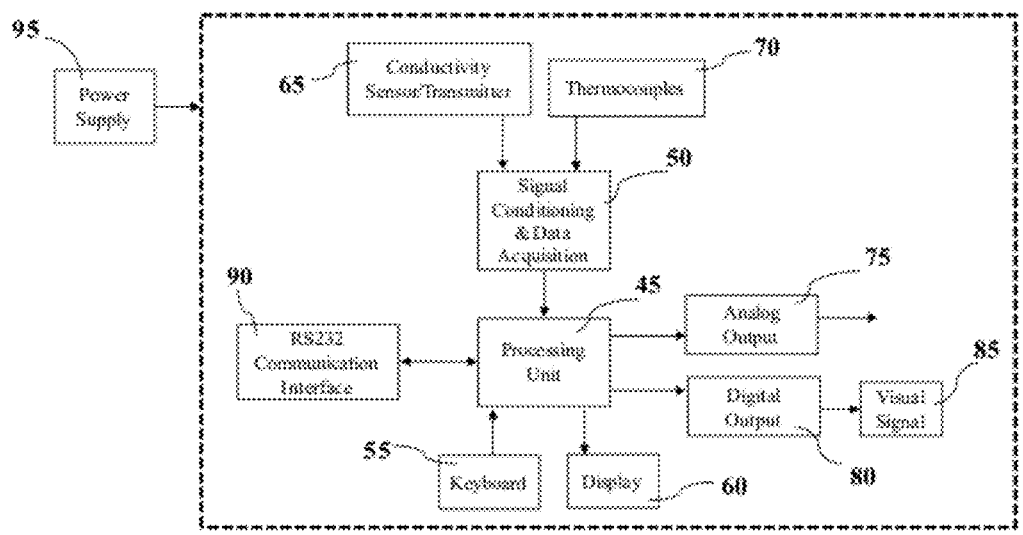
FIG. 2. Is an Illustration of the apparatus in the preferred embodiment.

The preferred embodiment of the apparatus conceived in this invention, presented in FIG. 2, consists of the following elements: (45) a processing unit board, (50) signal conditioning and data acquisition module board with for inputs, (55) a keyboard, (60) a display, (65) a toroidal electrical conductivity sensor, with a transmitter that uses a 4-20 mA output, (70) a thermocouple, (75) an analog output board of 4-20 mA, (80) a digital output board, (85) a visual signal, (90) a serial RS-232 communication interface, and (95) a power supply.

In the preferred embodiment of the apparatus, the signal conditioning and data acquisition board are used to receive the signal coming from the thermocouple and electrical conductivity transmitter and passing in a digital form to the processing unit.

The analog output board communicates with the processing unit, trough digital format to convert this digital signal to an analog signal of 4-20 mA proportional to biodiesel concentration.

The digital output board receives a signal coming from the processing unit that is the output from the alarm function. This signal is conditioning in the digital output board to be transmitted in a safe way using differential voltage.

The visual signal uses the signal from the digital output board to show the alarm status on-site.

The RS-232 Interface provides communication with a PC, modem, or another apparatus to transmit the current value of the biodiesel concentration and alarm signal.

Figure 3:
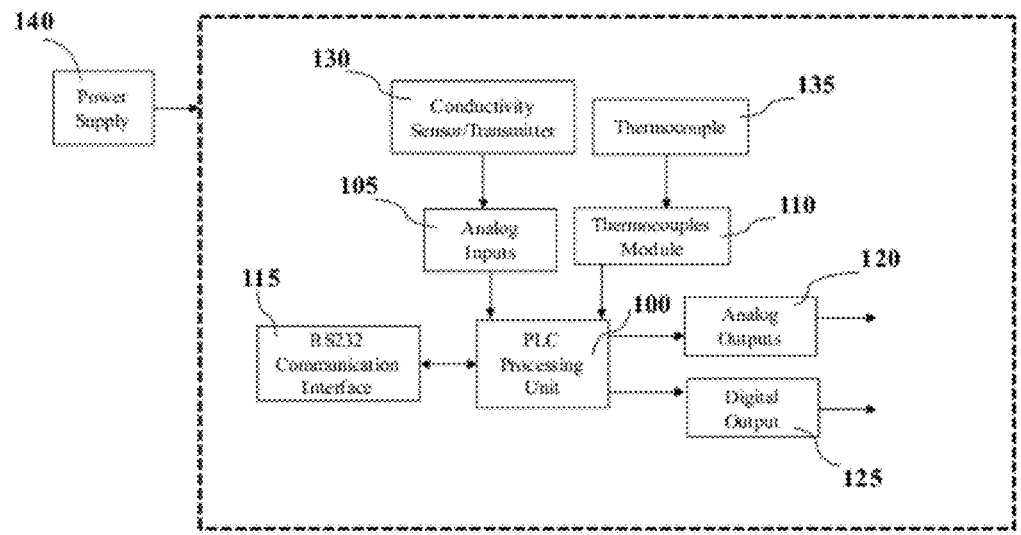
FIG. 3. Is an Illustration of other configuration using PLC in the preferred embodiment.

Another possible embodiment of the apparatus, is presented in FIG. 3, may consists of the following elements: (100) a Programmable Logic Controller (PLC) processor unit, (105) 4-20 mA analog inputs module for PLC, (110) thermocouple inputs module for PLC, (115) RS-232 serial communication module for PLC, (120) 4-20 mA analog outputs module for PLC, (125) a 24 volts digital outputs module for PLC, (130) a toroidal electrical conductivity sensor, with a transmitter that uses a 4-20 mA output, (135) a thermocouple, and (140) power supply.

The PLC processing unit executes the significance, calibration, estimation, delay, storage and alarm functions. Also have routines to allow the user to input the data for start-up operations in an easy way with a computer interface. The function may be executed also in an external PLC or PC that communicates with processing unit.

The analog input module receives the signal from the conductivity transmitter and communicates with the processor unit. The analog output module communicates with the processing unit, giving a 4-20 mA analog signal proportional to biodiesel concentration.

The digital output module communicates with the processing unit giving a signal proportional to the alarm function output.

The RS-232 Interface provides communication with a PC, modem, or another apparatus to access the programming interface from PLC, and eventually transmit the real time data from biodiesel concentration measurement.

Figure 4:
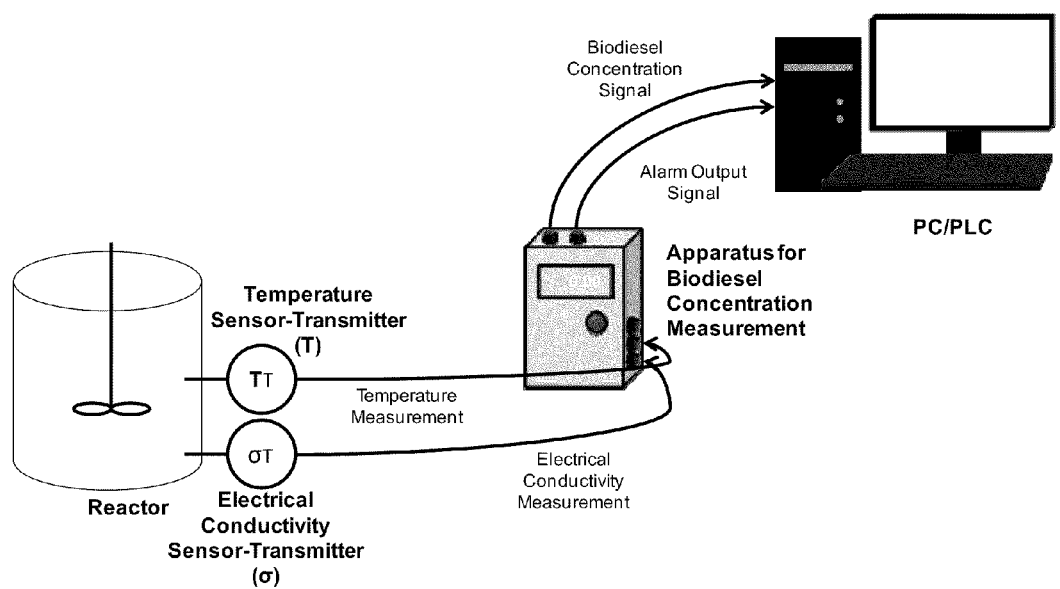
FIG. 4. Is an Illustration of typical configuration for biodiesel concentration measurement using the apparatus.

A typical configuration for biodiesel concentration measurement using the invention described above is presented in FIG. 4. This information could be used to feed a control algorithm that controls the reaction process or a monitoring process to assure quality of the reaction.

The invention claimed is:

1. A method of measuring and forecasting concentration of species during a reaction of a reacting mixture, the method comprising:
    measuring an electrical conductivity of species during a reaction of a reacting mixture;
    storing a vector value of the electrical conductivity of species;
    inputing the stored vector values into an estimation function and a deviation function;
    solving the estimation function to determine and forecast a value of a species concentration;
    solving the deviation function to set off an alarm.

2. The method of claim 1, wherein further comprising measuring environmental variables and building trajectory vectors that are input to the estimation function and deviation functions.

3. The method of claim 2, wherein the environmental variables are selected from a group comprising pressure, temperature, time, humidity, pH, and concentration.

4. The method of claim 3, wherein at least five data points are generated for every measured variable.

5. The method of claim 4, further comprising delaying the input of the measured variables for use in the step of storing the vector value.

6. The method of claim 1, wherein the estimation function is a feed-forward neural network.

7. The method of claim 6, wherein a standard feed-forward neural network has at least:
    an input layer, a hidden layer and an output layer.

8. The method of claim 7, wherein weights of the hidden layer are calculated using random numbers regularized.

9. The method of claim 7, wherein an activation function for the hidden layer is a sigmoid-like function.

10. The method of claim 7, wherein an activation function for the input and output layers is linear.

11. The method of claim 6, wherein the neural network is optimized using a greedy search modified for multiobjective optimization.

12. The method of claim 1, wherein the deviation function is a time based function with a model based on the measured variable trajectories that identifies a behavioral or a reaction behavior using pattern recognition techniques.

13. The method of claim 1, wherein the deviation function generates a nonlinear dynamic hybrid function that activates an alarm through a binary state based on a deviation from a desired reaction pattern.

14. The method of claim 1, further comprising a calibration function used to calculate coefficients of the estimation function using measured variables.

15. The method of claim 14, wherein the calibration function is used to calculate coefficients of the deviation function using the measured variables.

16. The method of claim 2, wherein the measured variables are determined by a significance evaluation function that is used in a start-up operation for an analysis of significant variables that are selected for an identification of concentration variations in the reaction.

17. The method of claim 14, where the coefficients are estimated based on kinetic parameters determined experimentally.

18. The method of claim 14, where the coefficients are estimated based on an experimental dynamic conductivity model.

19. An apparatus designed to execute the method of claim 1, the apparatus comprising:
    a plurality of sensors;
    an alarm set through a binary state;
    at least one display;
    at least one keyboard;
    a communication interface;
    analog/digital inputs;
    analog/digital outputs;
    at least one processing unit;
    at least one data acquisition module; and
    a storage unit.

20. The apparatus of claim 19, wherein the plurality of sensors comprise pressure, temperature, time, humidity, pH, concentration and electrical conductivity sensors.

21. The apparatus of claim 19, wherein the communication interface is through a serial standard RS232.

* * * * *